United States Patent [19]

Miller et al.

[11] Patent Number: 4,936,905

[45] Date of Patent: * Jun. 26, 1990

[54] SUBSTITUTED 2,6-SUBSTITUTED PYRIDINE COMPOUNDS HAVING HERBICIDAL ACTIVITY

[75] Inventors: Maria L. Miller, Manchester; Len F. Lee, St. Charles, both of Mo.; Mark G. Dolson, San Pablo, Calif.

[73] Assignee: Monsanto Company, St. Louis, Mo.

[*] Notice: The portion of the term of this patent subsequent to Dec. 6, 2005 has been disclaimed.

[21] Appl. No.: 184,855

[22] Filed: Apr. 22, 1988

Related U.S. Application Data

[63] Continuation-in-part of Ser. No. 861,379, May 9, 1986, abandoned.

[51] Int. Cl.$^5$ .................. C07D 213/55; C07D 213/34; C07D 213/69; A01N 43/40
[52] U.S. Cl. .......................................... 71/94; 546/14; 546/294; 546/296; 546/298; 546/322
[58] Field of Search ............... 546/296, 298, 294, 322, 546/14; 71/94

[56] References Cited

U.S. PATENT DOCUMENTS 4,789,395 12/1988 Lee et al. ................................. 71/94

*Primary Examiner*—Alan L. Rotman
*Attorney, Agent, or Firm*—James C. Bolding

[57] ABSTRACT

Disclosed herein are substituted pyridine-3-monocarboxylate compounds in which a substituent is bonded to the pyridine ring at the 5-position through an oxygen atom.

15 Claims, No Drawings

SUBSTITUTED 2,6-SUBSTITUTED PYRIDINE COMPOUNDS HAVING HERBICIDAL ACTIVITY

This is a continuation-in-part of copending application Ser. No. 861,379 filed May 9, 1986, now abandoned.

This invention relates to a new class of 2,6-substituted pyridinecarbox-ylic acid derivatives having a wide range of activity as herbicides.

Pyridine derivatives have, for many years, been investigated for use in the biological sciences. For example, 2,6-bis-(trifluoromethyl)-4-pyridinols have been found useful as herbicides and fungicides as disclosed in U.S. Pat. No. 3,748,334. Such compounds are characterized by substitution in the 4-position by a hydroxyl radical. In addition to the hydroxyl radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO patent No. 44,262 there are disclosed 2,6-dialkyl-3-phenylcarbamyl-5-pyridinecarboxylates and -5-cyano-compounds useful as herbicides. There is no disclosure of the 2-haloalkyl radicals nor any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4 position is occupied by a silver salt, U.S. Pat. No. 1,944,412 discloses that such compounds have been utilized in the production of X-ray pictures with intraveneous injection of such compounds.

Pyridine dicarboxylate compounds useful as herbicides are described in European Patent publication No. 133,612. These compounds have fluorinated methyl groups at the 2- and 6-positions and carboxylic acid derivative at the 3- and 5-positions.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

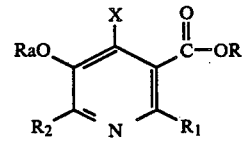

wherein:

R is selected from the group consisting of hydrogen, lower alkyl, lower alkenyl, lower alkynyl, haloalkyl, haloalkenyl;

$R_1$ and $R_2$ are independtly selected from fluorinated methyl and chlorofluorinated methyl radicals;

Ra is selected from lower alkyl, hydrogen and phenyl optionally substituted with one or more groups selected from methyl, methoxy, and chloro;

X is selected from hydrogen, hydroxy, alkoxy, phenylsulfonyloxy, phenylcarbonyloxy, or phenyloxyacetyloxy wherein the phenyl is optionally substituted with methyl or chloro; trialkylsilyl, lower alkyl, alkoxycarbonylalkoxy, alkoxycarbonyl, and a monovalent cation forming a salt of the hydroxy compound.

The term "alkyl" means herein both straight and branched chain radicals which include, but are not limited to, ethyl, methyl, n-propyl, 1-ethylpropyl, 1-methylpropyl, n-butyl, 2,2-dimethylpropyl, pentyl, isobutyl, isopropyl.

The term "lower alkyl" herein means an alkyl radical having 1 to 7 carbon atoms. The terms "lower alkenyl" and "lower alkynyl" herein mean alkenyl and alkynyl groups having 3 to 7 carbon atoms. Examples of such alkenyl groups include 2-propenyl, 2-butenyl, 3-butenyl, 2-methyl-2-propenyl, and the like. Examples of such lower alkynyl groups include 2-propynyl, and so forth.

The term "haloalkyl" is intended to mean lower alkyl radicals (as defined above) substituted with one or more halogen atoms; similarly, "haloalkenyl" is intended to mean a lower alkenyl group (as defined above) substituted with one or more halogen atoms.

The term "a monocalent cation forming a salt of the hydroxy compound" herein means the reaction product of a monovalent cation derived from a base and the 4-hydroxy pyridine compound. Typical cations include, but are not limited to, alkali metals such as sodium, potassium, and lithium, organic amines, and ammonium salts, sulfonium, phosphonium salts, and other monovalent salt complexes.

The term "fluorinated methyl" means herein methyl radicals having one, two, or three fluorine atoms attached thereto, the remaining substituents on the group being hydrogen atoms.

The term "chlorofluorinated methyl" means herein a methyl radical having at least one hydrogen replaced by fluorine and at least one other hydrogen replaced by chlorine, and includes such radicals as $CF_2Cl$, $CFCl_2$, and $CFClH$.

DETAILED DESCRIPTION OF THE INVENTION

The scheme shown below schematically depicts a method whereby certain pyridine monocarboxylate compounds of this invention may be prepared from compounds which are readily available commercially. In this scheme, a 3-ketoester of the formula shown in which Ra is aryl or lower alkyl is reacted with trifluoroacetonitrile in the presence of a base. Examples of suitable bases are potassium-t-butoxide, sodium dissolved in dimethyl ether, sodium acetate, and the like. The result of this reaction is a 2-(aryloxy- or alkoxy-)acetyl-3-amino-2-alkenoate ester; i.e., an enamine compound.

The enamine compound so produced is then reacted with an ester of a carboxylic acid of the formula shown wherein $R_2$ is selected from perfluorinated methyl, and perchlorofluorinated methyl. This reaction is carried out in the presence of two equivalents of a strong base, suitably lithium diisopropylamide. The reaction product is a substituted 1,3-dihydro-2-hydroxy-4-pyridone, which dehydrates readily when heated to form a 4-hydroxy-2-(trifluoromethyl)-6-(perfluorinated methyl or perchlorofluorinated methyl) -5-(aryloxy- or alkoxy-)-3-pyridinecarboxylate of the present invention.

The 4-hydroxy pyridine compound shown in Formula A may be converted to a 4-alkoxy compound of this invention by alkylation with an alkyl halide in the presence of a base. Alkali metal carbonates or hydroxides, amines, and the like, are examples of suitable bases which promote the alkylation reaction.

The 4-hydroxy pyridine compound shown in Formula A may be converted to a 4-hydrogen compound shown in Formula C of this invention by reacting its corresponding tosylate (Formula B) with lithium dimethyl copper. The 4-hydrogen compound so produced is then reacted with a strong base, suitably lithium diisopropylamide, followed by alkylation with an alkyl halide, trialkylsilyl chloride or carbon dioxide to produce compound of Formula D.

Compounds of this invention wherein X is alkyl may also be prepared by making a 4-alkyl-5-halo-3-pyridinecarboxylate and reacting this compound with an alkoxide ion. Preparation of a pyridine compound of this invention by this route is shown in Example 39.

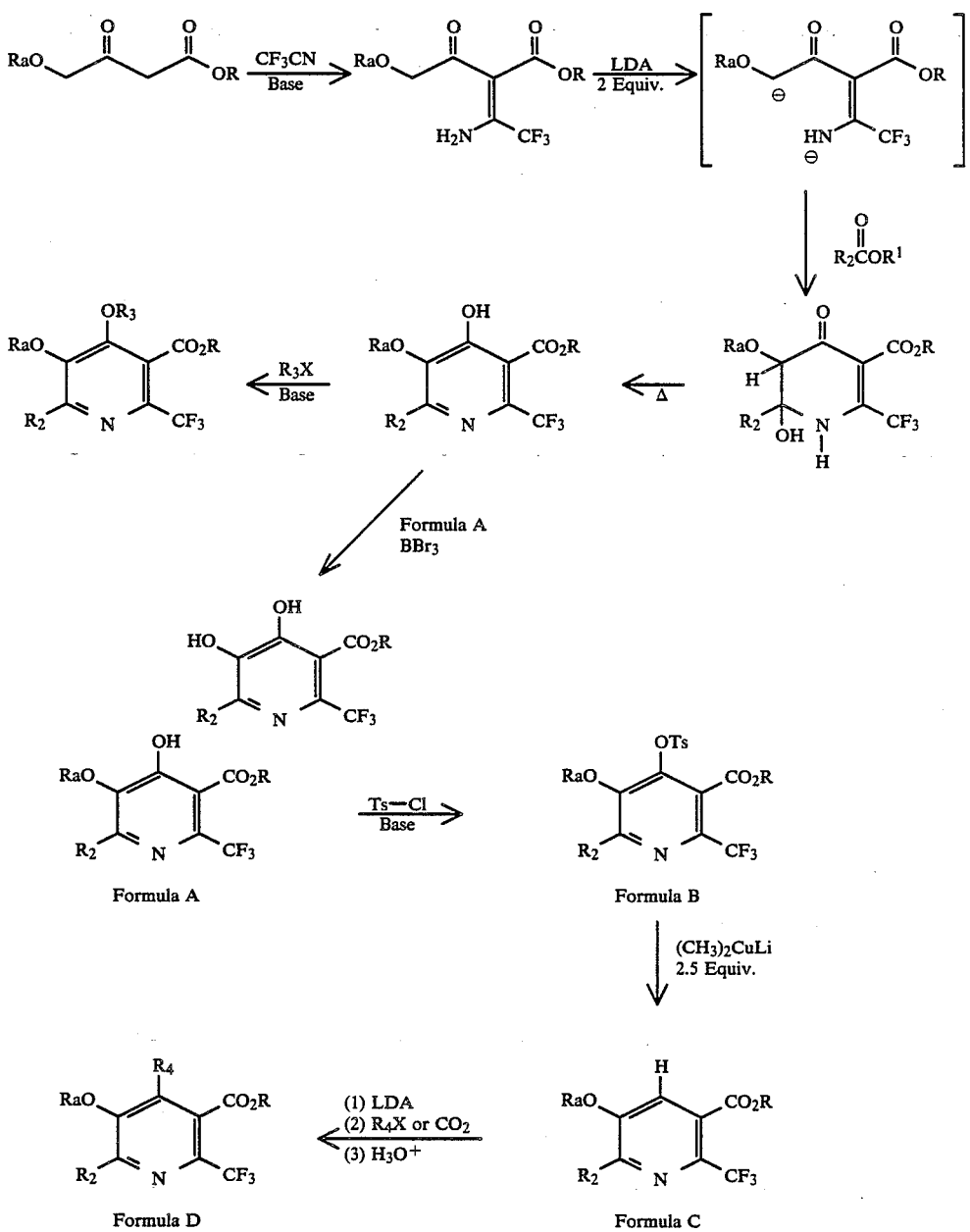

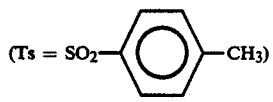

(R₄ = alkyl, CO₂H, (CH₃)₃Si)

Preparation of further compounds of this invention will become clear by reference to the scheme in conjunction with the following examples.

As used throughout the specification, including the Examples, the following abbreviations have the following meanings:

LDA - lithium diisopropylamide
THF - tetrahydrofuran
DME - dimethyl ether
DMF - N,N-dimethylformamide
MCPBA - m-chloroperbenzoic acid
HPLC - high pressure liquid chromatography
TLC - thin layer chromatography
n-BuLi - n-Butyl lithium
DMSO - dimethyl sulfoxide
Pd/C - hydrogenation catalyst which is palladium deposited on finely-divided carbon
TsCl - tosyl chloride
RT - room temperature
(CH₃)₂CuLi - lithium dimethyl copper As used in the following Examples, the terms "workup as usual", or "normal workup", or equivalent language refer to the process of washing the organic extract with brine, drying by pouring through a cone of anhydrous sodium sulfate, and concentrating in vacuo.

EXAMPLE A1

Butanoic acid,4-ethoxy-3-oxo,ethyl ester.

In a 3-necked round bottomed flask equipped with a magnetic stirring bar and a Friedrich condenser was dissolved 8.4 g (0.364 mol) of sodium in 100 mL of absolute ethanol. To the resulting solution was added 100 mL of dry DMSO. The mixture was then treated at 20° C. with external cooling and stirring with 23.76 g (19.5 mL, 0.144 mol) of ethyl γ-chloroacetoacetate. The mixture turned to a cloudy yellow-orange color. After 54 hours at room temperature the reaction was poured into an ice-cooled solution of 20 mL of concentrated HCl and 400 mL of H₂O. The mixture was extracted with CH₂Cl₂ (3×100 mL) and the combined organics were dried (MgSO₄) and reduced in vacuo to give a yellow oil which was distilled to give 19 g (76%) of product as a colorless liquid: bp 102°–106° C. (11 mm Hg); $n_D^{25}$ 1.4271.

Elemental Analysis: C H
Calculated 55.16 8.10
Found 55.21 8.12

EXAMPLE A2

2-Butenoic acid,3-amino-2-(2-ethoxy-1-oxoethyl)-4,4,4-trifluoro-,ethyl ester.

Into a magnetically stirred mixture of 8.73 g (0.05 mol) of product of Example A1 and 0.17 g (1.5 mmol) of potassium t-butoxide at 25° C. was passed trifluoroacetonitrile. The mixture turned light yellow and a white precipitate formed. The reaction mixture was monitored by thin layer chromatography on silica gel using ethyl acetate:cyclohexane eluent, 1:4 V/V. After 48 hours, the mixture contained a major product ($R_f$ 0.67) and no detectable amount of starting material ($R_f$ 0.78). The semi-solid, light yellow oil was distilled [Kugelrohr 85°–110° C. (0.3 mm Hg)] to give 10.56 g (79%) of product as a light yellow oil: $n_D^{25}$ 1.4632.

Elemental Analysis: C H N
Calculated 44.61 5.24 5.20
Found 44.67 5.25 5.19

EXAMPLE B1

Butanoic acid, 3-oxo-4-phenoxy-,ethyl ester.

To a mechanically stirred suspension of 64.3 g (1.5 mol) of NaH (56% oil dispersion) in 600 mL of dry DMSO was added (with cooling) 56.5 g (0.6 mol) of phenol in 300 mL of dry DMSO followed by dropwise addition of 98.8 g (81 mL, 0.6 mol) of ethyl-γ-chloroacetoacetate in 100 mL of dry DMSO. After 24 hours at room temperature the mixture was poured into 1.5 L of 0° C. H₂O. The resulting mixture was washed with hexane and then the pH was adjusted to 7 with 40% aqueous H₃PO₄. The mixture was extracted with CH₂Cl₂ (3x). The extracts were dried (MgSO₄) and concentrated in vacuo. The remaining DMSO was removed by Kugelrohr distillation at 70° C. (5 mm Hg). The residue was fractionally distilled through a 6-inch Vigreux column affording 62.56 g (47%) of product as a colorless liquid: bp 134° C. (0.85 mm Hg); $n_D^{25}$ 1.5086.

Elemental Analysis: C H
Calculated 64.85 6.35
Found 64.79 6.36

EXAMPLE B2

Butanoic acid, 2-(1-amino-2,2,2-trifluoroethylidene)-3-oxo-4-phenoxy-,ethyl ester.

Through a magnetically stirred solution of 11.1 g (0.05 mol) of product of Example B1 and 0.17 g (1.5 mmol) of potassium t-butoxide in 40 mL of dry THF was passed CF₃CN at 25° C. The reaction mixture was monitored by thin layer chromatography on silica gel, using ethyl acetate:cyclohexane 1:20 V/V as eluent. When a major product ($R_f$ 0.06) appeared and no detectable amount of starting material ($R_f$ 0.15) remained, the solvent was evaporated in vacuo and the crude material was filtered through silica gel using ethyl acetate as eluent. Solvent was evaporated in vacuo and the residual solid was recrystallized from ether:hexane to afford 9.33 g (59%) of product as a light yellow solid: mp 58°–62° C.

Elemental Analysis: C H N
Calculated 53.00 4.45 4.41
Found 53.08 4.46 4.10

EXAMPLE C

2-Butenoic acid, 3-amino-2-(2-methoxy-1-oxoethyl)-4,4,4-trifluoro-, methyl ester.

Into a magnetically stirred solution of 14.6 g (0.1 mol) of commercially available methyl methoxyacetoacetate and 0.1 g (0.9 mmol) of potassium t-butoxide in 10 mL of dry THF was passed 11.4 g (0.12 mol) of CF$_3$CN at room temperature for 48 hours. The reaction mixture was poured into 5% HCl (aq), extracted with ether (2x), and the ether phase was dried (MgSO$_4$) and concentrated in vacuo. The residue was distilled [Kugelrohr, 80°–85° C. (0.8 mm Hg)] affording 18.65 g (79%) of product as a light yellow semi-solid: mp 26°–30° C.

Elemental Analysis: C H N
Calculated 39.84 4.18 5.81
Found 39.86 4.21 5.81

EXAMPLE D1

Butanoic acid, 4-(4-chlorophenoxy)-3-oxo-, ethyl ester.

To a mechanically stirred suspension of 64.3 g (1.5 mol) of NaH (56% oil dispersion) in 600 mL of dry DMSO was added (with cooling) 77.14 g (59 mL, 0.6 mol) of 4-chlorophenol in 300 mL of dry DMSO followed by dropwise addition of 98.8 g (81 mL, 0.6 mol) of ethyl γ-chloroacetoacetate in 100 mL of dry DMSO. After 24 h at RT, the mixture was poured into 4 L of 0° C. H$_2$O, the resulting mixture was washed with hexane and then the pH was adjusted to 5–7 with 85% H$_3$PO$_4$ (a light yellow solid precipitated). The mixture was extracted with Et$_2$O (2x). The extracts were dried (MgSO$_4$), and concentrated in vacuo and the resulting residue was recrystallized twice, first from ether:cyclohexane followed by ethyl acetate:hexane affording 69.18 g (45%) of product as a yellow solid: mp 52°–55° C.

Elemental Analysis: C H Cl
Calculated 56.15 5.11 13.81
Found 56.13 5.12 13.81

EXAMPLE D2

Butanoic acid, 2-(1-amino-2,2,2-trifluoro-ethylidene)-3-oxo-4-(4'-chlorophenoxyl)-, ethyl ester.

Through a magnetically stirred solution of 25.67 g (0.1 mol) of product of Example D1 and 0.34 g (0.003 mol) of potassium t-butoxide in 200 mL of dry THF was passed CF$_3$CN at 25° C. After 9.8 g (0.103 mol) of CF$_3$CN had been added, the reaction was complete. Solvent was evaporated in vacuo and the residue was recrystallized from hot Et$_2$O (200 mL) affording 20.39 g (58%) of product as a light beige solid: mp 108°–110° C.

Elemental Analysis: C H Cl N
47.81 3.73 10.08 3.98
47.86 3.73 10.04 3.95

EXAMPLE 1

3-Pyridinecarboxylic acid, 5-ethoxy-4-hydroxy-2,6-bis(trifluoromethyl)-,ethyl ester.

To 60 mL of dry DME, cooled to −78° C., was added 1.55M n-butyllithium in hexane (60 mL, 0.093 mol) followed by 8.7 g (12 mL, 0.086 mol) of diisopropylamine. After stirring at −78° C. for 30 min, a solution of 10.76 g (0.04 mol) of product from Example A2 in 10 mL of dry DME was added. The reaction turned dark red and a brown precipitate formed. After stirring at −78° C. for 1 hour, 18.5 g (16 mL, 0.134 mol) of ethyl trifluoroacetate was added and a precipitate formed which made stirring difficult. This reaction mixture was left at −78° C. for 1 hour, then warmed to room temperature (the precipitate disappeared) and stirred overnight. The resulting solution was poured into 300 mL of 0° C. H$_2$O and extracted with Et$_2$O. The ether layer was extracted again with 20% aq. K$_2$CO$_3$ and H$_2$O. All the combined aqueous phases were acidified with concentrated HCl while being cooled in a 0° C. bath, causing an oil to separate. The mixture was extracted with Et$_2$O (2x) and the combined Et$_2$O layers were dried (MgSO$_4$) and reduced in vacuo affording a thin orange oil. The remaining DME was removed by Kugelrohr distillation at 50° C. (0.3 mm Hg). The residue was heated to 140° C. for 30 minutes followed by Kugelrohr distillation at 100° C. (0.3 mm Hg) affording 7.8 g (57%) of product as a light yellow semi-solid: mp 24°–25° C. Crystallization from Et$_2$O/hexane afforded an analytical sample of product as a white solid: mp 26°–27° C.

Elemental Analysis: C H N
Calculated 41.51 3.19 4.03
Found 41.38 3.20 4.00

EXAMPLE 2

3-Pyridinecarboxylic acid, 4-hydroxy-5-phenoxy-2,6-bis(trifluoromethyl)-,ethyl ester.

To 60 mL of dry DME at −78° C. was added 60 mL (0.093 mol) of 1.55 M n-butyllithium in hexane followed by 8.7 g (12 mL, 0.086 mol) of diisopropylamine. After stirring at −78° C. for 30 min, a solution of 12.68 g (0.04 mol) of product of Example B2 in 10 mL of dry DME was added. The reaction turned yellowish-brown and a yellow precipitate formed. After stirring at −78° C. for 1 hour, 18.5 g (16 mL, 0.134 mol) of ethyl trifluoroacetate was added and a brown homogeneous solution slowly formed. This was left stirring at +78° C. for 1 hour, then warmed to room temperature and stirred overnight. The reaction mixture was poured into 300 mL of 0° C. H$_2$O and was washed with Et$_2$O. The ether layer was stirred overnight with 20% aq. K$_2$CO$_3$, separated and extracted with H$_2$O. The aqueous phases were combined and acidified with conc. HCl while being cooled in a 0° C. bath (a light yellow solid precipitated out) and were extracted with Et$_2$O (2x). The combined Et$_2$O layers were dried (MgSO$_4$) and solvent evaporated in vacuo affording a thin orange oil. The remaining DME was removed by Kugelrohr distillation at 50° C. (0.3 mm Hg) affording a sticky orange-yellow solid which was washed with hexane affording 7.25 g (44%) of the intermediate ethyl 6-hydroxy-4-oxo-5-phenoxy-1,4,5,6-tetrahydro-2,6-bis-(trifluoromethyl)-3-pyridinecarboxylate as a white solid: mp 148°–151° C.

A portion of this solid (2.4 g, 5.8 mmol) was heated to 130° C. for 20 minutes followed by Kugelrohr distillation at 105°–150° C. (0.5 mm Hg) affording 2.12 g (88.3%) of product as a white solid: mp 79°–81° C.

Elemental Analysis: C H N
Calculated 48.62 2.81 3.54
Found 48.36 2.77 3.52

EXAMPLE 3

3-Pyridinecarboxylic acid, 5-(4-chlorophenoxy)-4-hydroxy-2,6-bis(trifluoromethyl)-,ethyl ester.

This compound was prepared as described in Example 2. The product of Example D2 was reacted with LDA and ethyl trifluoroacetate affording the intermediate ethyl 5-(4-chlorophenoxy)-6-hydroxy-4-oxo-1,4,5,6-tetrahydro-2,6-bis(trifluoromethyl)-3-pyridinecarboxylate. This intermediate was then heated to 130° C. for 20 minutes followed by distillation affording 85% yield of product as a white solid: mp 62°–64° C.
Elemental Analysis: C H N Cl
Calculated 44.72 2.35 3.26 8.25
Found 44.80 2.38 3.26 8.20

EXAMPLE 4

3-Pyridinecarboxylic acid,4,5-dihydroxy-2,6-bis(trifluoromethyl)-,ethyl ester.

To a solution of 3.19 g of product of Example 1 in 50 mL of $CH_2Cl_2$ was added 30 mL (0.03 mol) of 1.0 M $BBr_3$ solution in $CH_2Cl_2$. The reaction mixture was stirred at room temperature overnight and then poured into 0° C. $H_2O$. The $CH_2Cl_2$ phase was separated and the aqueous layer was extracted with $CH_2Cl_2$ (2x). The combined organics were treated with charcoal and $Na_2SO_4$, filtered and concentrated in vacuo. The residue was recrystallized from hot hexane affording 1 g (31.3%) of the product as a yellow solid: mp 97°–100° C.
Elemental Analysis: C H N
Calculated 37.63 2.21 4.39
Found 37.67 2.24 4.37

EXAMPLE 5

3-Pyridinecarboxylic acid,4,5-dihydroxy-2,6-bis(trifluoromethyl)-,(1.1 hydrate).

The aqueous layer described in Example 4 was extracted again with ethyl acetate (2x). The combined organics were treated with charcoal and $Na_2SO_4$, filtered and concentrated in vacuo. The residue was washed with $CH_2Cl_2$ and dried in vacuo affording 1.05 g (36%) of the 1.1 hydrate as a beige hygroscopic solid: mp 214°–220° C. (dec.).
Elemental Analysis: C H N
Calculated 30.90 1.69 4.50
Found 30.39 1.30 4.42

EXAMPLE 6

3-Pyridinecarboxylic acid,5-ethoxy-4-{[(4-methylphenyl)sulfonyl]oxy}-2,6-bis(trifluoromethyl)-,ethyl ester.

To an $Et_2O$ solution of 13.88 g (0.04 mol) of product from Example 1 was added 3.16 g (3.2 ml, 0.04 mol) of pyridine followed by 7.63 g (0.04 mol) of p-toluenesulfonyl chloride. The reaction mixture was stirred at room temperatue for 2 hours and filtered, and the filtrate was washed with 20% aqueous $K_2CO_3$. The organic layer was dried ($MgSO_4$) and concentrated in vacuo. The residue was recrystallized from hexane affording 11.45 g (57%) of product as a beige solid: mp 55°–57° C.
Elemental Analysis: C H N S
Calculated 45.51 3.42 2.79 6.39
Found 45.56 3.45 2.83 6.56

EXAMPLE 7

3-Pyridinecarboxylic acid,5-ethoxy-4-{(4-methoxyphenyl)carbonyl]oxy}-2,6-bis(trifluoromethyl)-,ethyl ester.

As above, product of Example 1 (3.47 g, 0.01 mol), p-anisoyl chloride (1.71 g, 0.01 mol) and pyridine (0.79 g, 0.01 mol) were reacted affording 3.54 g (74%) of product as a beige solid: mp 78°–82° C.
Elemental Analysis: C H N
Calculated 49.90 3.56 2.91
Found 50.10 3.58 2.88

EXAMPLE 8

3-Pyridinecarboxylic acid,4-{[(4-chlorophenoxy)acetyl]oxy}-5-ethoxy-2,6-bis(trifluoromethyl)-,ethyl ester.

This compound was prepared as described above; product of Example 1 (3.47 g, 0.01 mol), p-chlorophenoxyacetyl chloride (2.05 g, 0.01 mol) and pyridine (0.79 g, 0.01 mol) were reacted affording 3.6 g (72%) of product as a beige solid: mp 59°–61° C.
Elemental Analysis: C H N Cl
Calculated 46.57 3.13 2.72 6.87
Found 46.64 3.15 2.74 6.89

EXAMPLE 9

3-Pyridinecarboxylic acid,4-{[phenyl carbonyl]oxy}-5-ethoxy-2,6-bis(trifluoromethyl)-, ethyl ester.

As above, product of Example 1 (9.68 g, 0.028 mol), benzoyl chloride (3.92 g, 3.2 mL, 0.028 mol) and pyridine (2.21 g, 2.3 mL, 0.028 mol) were reacted affording 9.85 g (78%) of product as a white solid: mp 99°–100° C.
Elemental Analysis: C H N
Calculated 50.56 3.35 3.10
Found 50.71 3.42 3.18

EXAMAPLE 10

3-Pyridinecarboxylic acid,4-{[(2,4-dichlorophenoxy)acetyl]oxy}-5-ethoxy-2,6-bis(trifluoromethyl)-, ethyl ester.

As above, product of Example 1 (3.47 g, 0.01 mol), 2,4-dichlorophenoxy acetyl chloride (2.41 g, 0.01 mol) and pyridine (0.79 g, 0.01 mol) were reacted affording 1.08 g (20%) of product as a beige solid: mp 79°–82° C.
Elemental Analysis: C H N
Calculated 43.66 2.75 2.55
Found 44.05 2.78 2.70

EXAMPLE 11

2-Pyridinecarboxylic acid,5-ethoxy-2,6-bis(trifluoromethy)-,ethyl ester.

To a −20° C. mechanically-stirred mixture of 19 g (0.1 mol) of CuI in 270 mL of anhydrous $Et_2O$ was added slowly 167 mL (0.2 mol) of 1.2 M methyllithium in $Et_2O$. The resulting solution was stirred at −20° C. for 30 min, then cooled to −78° C. followed by an addition of 20.04 g (0.04 mol) of product of Example 6 in 100 mL of anhydrous $Et_2O$. The resulting orange mixture was stirred at −78° C. for 15 min, then warmed slowly to 0° C. whereupon formation of a yellow precipitate was observed. The reaction was stirred at 0° C. for 1 h, poured into a 0° C. solution of 50% aqueous $NH_4OH$ and extracted with $Et_2O$ (2x); the combined organics were washed with a saturated solution of NaCl, dried ($MgSO_4$) and reduced in vacuo. The residue was Kugelrohr distilled affording 10.97 g (83%) of product as a colorless oil: bp 85°–90° C. (0.6 mm Hg); $n_D^{25}$ 1.4290.
Elemental Analysis C H N
Calculated 43.51 3.35 4.23
Found 43.55 3.35 4.19

EXAMPLE 12

3-Pyridinecarboxylic acid, 5-ethoxy-4-(trimethylsilyl)-2,6-bis(trifluoromethyl)-,ethyl ester.

To 10 mL (0.013 mol) of 1.55 M n-BuLi in hexane followed by 1.21 g (1.7 mL, 0.012 mol) of diisopropylamine. After stirring at −78° C. for 30 min a solution of 3.31 g (0.01 mol) of product of Example 11 in 10 mL of dry THF was added. The reaction mixture turned dark purple and was stirred at −78° C. for 15 min. Chlorotrimethylsilane (4.4 g, 0.04 mol) was added and the reaction mixture was stirred at −78° C. for ½ hour, then warmed to room temperature poured into 0° C. $H_2O$, and extracted with ether (2x). The ether extracts were dried ($MgSO_4$) and concentrated in vacuo. The residue was purified by HPLC using 2% ethyl acetate:cyclohexane as eluting solvent, followed by distillation (Kugelrohr) affording 1.7 g (42%) of product as a white solid: bp 90° C. (0.3 mm Hg); mp 29°-31° C.

Elemental Analysis: C H N
Calculated 44.66 4.75 3.47
Found 44.79 4.75 3.48

EXAMPLE 13

3-Pyridinecarboxylic acid, 5-ethoxy-4-ethyl-2,6-bis(trifluoromethyl)-,ethyl ester.

This compound was prepared as described in Example 12. The product of Example 11 (3.31 g, 0.01 mol) and $CH_3I$ (5.68 g, 2.5 mL, 0.04 mol) were reacted affording 3.36 g of a dark brown oil. The crude product was purified by HPLC using 10% ethyl acetate: cyclohexane as eluting solvent, followed by distillation (Kugelrohr) affording 1.51 g (42%) of product as a colorless oil: bp 70°-80° C. (0.2 mm Hg); $n_D^{25}$ 1.4283; and 0.89 g (27%) of unreacted starting material. (Example 11)

Elemental Analysis: C H N
Calculated 46.80 4.21 3.90
Found 46.88 4.30 3.87

EXAMPLE 14

3-Pyridinecarboxylic acid, 4-hydroxy-5-methoxy-2,6-bis(trifluoromethyl)-,methyl ester.

To 60 mL of dry DME cooled to −78° C. was added n-BuLi in hexane (55 mL, 0.093 mol) followed by 8.7 g (12 mL, 0.086 mol) of diisopropylamine. After stirring at −78° C. for 30 min, the reaction mixture was treated with a solution of 9.44 g (0.04 mol) of product of Example C in 30 mL of dry DME. The reaction mixture turned dark red and a yellowish precipitate formed. After stirring at −78° C. for 1 hour, 18.5 g (16 mL, 0.134 mol) of ethyl trifluoroacetate was added. A brown precipitate formed which made stirring difficult. This reaction mixture was left at −78° C. for 1 hour, then warmed to room temperature whereupon the precipitate disappeared. After stirring at room temperature for 2½ hours the reaction mixture turned dark green and a precipitate started to form. The resulting reaction mixture was poured into 0° C. $H_2O$ and washed with $Et_2O$. The EtzO layer was extracted again with 20% $K_2CO_3$ and $H_2O$ (2x). All aqueous phases were combined and acidified with concentrated HCl, causing an oil to separate. The mixture was extracted with $Et_2O$ (2x) and the combined $Et_2O$ layers were dried ($MgSO_4$) and reduced in vacuo affording a thin orange oil. The remaining DME was removed by Kugelrohr distillation at 60° C. (0.5 mm Hg) and the residue was heated to 130° C. for ½ hour followed by Kugelrohr distillation [bp 80°-90° C. (0.4 mm Hg)] affording the product (60% yield) as a light yellow solid: mp 74°-77° C.

Elemental Analysis: C H N
Calculated 37.63 2.21 4.39
Found 37.70 2.28 4.37

EXAMPLE 15

3-Pyridinecarboxylic acid, 6-(chlorodifluoromethyl)-4-hydroxy-5-methoxy-2-(trifluoromethyl),methyl ester (0.25 hydrate).

This compound was prepared as described in Example 14; 24.1 g (0.1 mol) of product of Example C, 21.21 g (29.4 mL, 0.21 mol) of diisopropylmaine, n-BuLi in hexane (142 mL, 0.22 mol, 1.55 M) and 53 g (0.335 mol) of ethyl chlorodifluoroacetate were reacted affording 48.61 g of a semi-liquid solid. This crude solid was heated to 120° C. for ½ hour and distilled (Kugelrohr) affording 20.66 g (62%) of product as a light yellow solid: bp 70°-110° C. (0.6 mm Hg); mp 67°-69° C.

Elemental Analysis: C H N Cl
Calculated 35.31 2.22 10.42 4.12
Found 35.31 2.37 10.44 4.16

EXAMPLE 16

3-Pyridinecarboxylic acid, 5-ethoxy-4-[(ethoxycarbonyl)methoxy]-2,6-bis(trifluoromethyl)-, ethyl ester.

A mixture of 17.35 g (0.05 mol) of product of Example 1, 12.52 g (8.3 mL, 0.075 mol) of ethyl bromoacetate and 6.9 g (0.05 mol) of $K_2CO_3$ in 50 mL of acetone was refluxed for 3 days. The reaction mixture was then cooled to room temperature. The solvent was removed in vacuo, and the residue was dissolved in $Et_2O$. The ether solution was washed with $H_2O$, dried ($MgSO_4$) and concentrated in vacuo affording 22 g of a brown oil. The crude product was purified by Kugelrohr distillation affording 17.19 g (63%) of product as a yellow oil. A portion (8.1 g) of the distilled product was HPLC using 10% ethyl acetate:cyclohexane as eluting solvent affording 7.53 g of an analytical sample as light yellow oil: $n_D^{25}$ 1.4330.

Elemental Analysis: C H N
Calculated 44.35 3.95 3.23
Found 44.31 3.98 3.35

EXAMPLE 17

3-Pyridinecarboxylic acid,5-ethoxy-4-(1-methylethoxy)-2,6-bis(trifluoromethyl)-,ethyl ester.

This compound was prepared as described in Example 16; 3.47 g (0.01 mol) of product of Example 1 was treated with 1.4 g (0.01 mol) of $K_2CO_3$ and 13.6 g (8 mL, 0.08 mol) of 2-iodopropane in 10 mL of refluxing acetone for 2 days affording 3.27 g of a brown oil. The crude material was purified by Kugelrohr distillation affording 2.88 g (74%) of product as a pale yellow oil: bp 80°-90° C. (0.35 mm Hg); $n_D^{25}$ 1.4239;

Elemental Analysis: C H N
Calculated 46.28 4.40 3.60
Found 46.11 4.46 3.60

EXAMPLE 18

3-Pyridinecarboxylic acid,
5-methoxy-4-(1-methylethoxy)-2,6-bis(trifluoromethyl)-, 1-methylethyl ester.

This compound was prepared as described in Example 16; 6.38 g (0.02 mol) of product of Example 14 was treated with 27.2 g (16 mL, 0.16 mol) of 2-iodopropane and 2.76 g (0.02 mol) of $K_2CO_3$ in 100 mL of refluxing acetone affording 7.64 g of a brown oil. The oil was Kugelrohr distilled at 75°–85° C. (0.45 mm Hg) affording 6.36 g of a product that was further purified by HPLC using 8% ethyl acetate:cyclohexane as eluting solvent giving 5.16 g (66%) of product as a light yellow oil: $n_D^{25}$ 1.4272.

Elemental Analysis: C H N
Calculated 46.28 4.40 3.60
Found 46.31 4.40 3.35

EXAMPLE 19

3-Pyridinecarboxylic acid,
6-(difluoromethyl)-4-hydroxy-5-methoxy-2-(trifluoromethyl)-, methyl ester.

To a solution of 6.71 g (0.02 mol) of produce of Example 15 and 4.04 g (5.6 mL, 0.04 mol) of triethylamine in 100 mL of ethanol was added 0.34 g of 10% Pd/C (57% $H_2O$). The resulting mixture was heated to 70° C. under 61 psi of $H_2$ (g) for 72 hours. The reaction mixture was filtered through celite and concentrated in vacuo. The residue was dissolved in $Et_2O$ and poured into 10% HCl (aq). The aqueous layer was extracted with $Et_2O$ (2x) and the combined $Et_2O$ layers were dried ($MgSO_4$). The solvent was removed in vacuo affording 5.91 g (98%) of product as a beige solid. A sample for elemental analysis was recrystallized from ether/hexane affording a light beige solid: mp 62°–64° C.

Elemental Analysis: C H N
Calculated 39.88 2.68 4.65
Found 39.77 2.57 4.62

EXAMPLE 20

3-Pyridinecarboxylic acid,
5-methoxy-4-{[(4-methylphenyl)sulfonyl]oxy}-2,6-bis(trifluoromethyl)-,methyl ester.

To a mixture of 6.55 g (0.02 mol) of product of Example 14 in 50 mL of anhydrous $Et_2O$ was added 1.66 g (1.7 mL, 0.02 mol) of pyridine followed by 4 g (0.02 mol) of TsCl. The reaction mixture was stirred at room temperature for 72 hours, filtered, poured into $H_2O$ and extracted with $Et_2O$ (2x). The combined organic layers were dried ($MgSO_4$), concentrated in vacuo and the residue (9.5 g) was purified by HPLC using 10% ethyl acetate/cyclohexane as eluting solvent affording 8.17 g (86%) of product as a beige solid: mp 111°–113° C.

Elemental Analysis: C H N S
Calculated 43.14 2.77 2.96 6.77
Found 43.34 3.02 2.98 6.84

EXAMPLE 21

3-Pyridinecarboxylic acid, 5-methoxy-4-(1-methylethoxy)-2,6-bis(trifluoromethyl)-,methyl ester (0.25 hydrate).

To a solution of 5.22 g (0.016 mol) of product of Example 14 in 40 mL of DMF was added 15.6 g (0.166 mol) of KF·2H₂O followed by 5.56 g (0.032 mol) of 2-iodopropane. The reaction mixture was stirred at room temperature for 72 hours, poured into $H_2O$, extracted with $Et_2O$. The $Et_2O$ layer was washed with $H_2O$ (3x), saturated NaCl (aq) and then dried ($MgSO_4$). The solvent was removed in vacuo affording 3.45 g of an orange oil that was purified by HPLC using 8% ethyl acetate:cyclohexane as eluting solvent affording 2 g (34%) of product as a light yellow oil: $n_D^{25}$ 1.4232.

Elemental Analysis: C H N
Calculated 42.69 3.72 3.83
Found 42.78 3.78 3.69

EXAMPLE 22

3-Pyridinecarboxylic acid,
4-{[(4-chlorophenoxy)acetyl]oxy}-5-methoxy-2,6-bis(trifluoromethyl)-,methyl ester.

This compound was prepared as described in Example 20; 3.19 g (0.01 mol) of product of Example 14 was treated with 0.79 g (0.81 mL, 0.01 mol) of pyridine and 2.05 g (0.01 mol) of p-chlorophenoxyacetyl chloride for 2 hours affording 5.23 g of a light yellow solid. The solid was recrystallized from hot ether/hexane (3.93 g) followed by HPLC using 50% ethyl acetate:cyclohexane as eluting solvent affording 3.29 g (68%) of product as a beige solid: mp 75°–77° C.

Elemental Analysis: C H N Cl
Calculated 44.33 2.48 2.87 7.27
Found 44.31 2.56 2.83 7.24

EXAMPLE 23

3-Pyridinecarboxylic acid,
6-(chlorodifluoromethyl)-5-ethoxy-4-hydroxy-2-(trifluoromethyl)-, ethyl ester (0.25 hydrate).

This compound was prepared as described in Example 14; 26.9 g (0.1 mol) of product of Example A2 was treated with 0.21 mol of LDA followed by 53 g (0.355 mol) of ethyl chlorodifluoroacetate affording 33.02 g of a brown oil. The oil was heated to 130° C. for ½ hour followed by Kugelrohr distillation affording 24.05 g (65%) of product as a yellow oil: bp 110°–120° C. (2 mm); $n_D^{25}$ 1.4532.

Elemental Analysis: C H N Cl
Calculated 39.15 3.15 3.80 9.62
Found 39.10 3.32 3.79 9.68

EXAMPLE 24

3-Pyridinecarboxylic acid,
5-methoxy-2,6-bis(trifluoromethyl).

To a −20° C. mechanically stirred mixture of 15.5 g (0.0814 mol) of CuI in 100 mL of anhydrous $Et_2O$ was added slowly 136 mL (0.1625 mol) of 1.2M MeLi in $Et_2O$. The resulting solution was stirred at −20° C. for ½ hour, then cooled to −78° C. followed by addition of 15.4 g (0.0325 mol) of product of Example 20 in 200 mL of anhydrous $Et_2O$. The resulting orange mixture was stirred at −78° C. for 15 min, then warmed slowly to 0° C. whereupon formation of a yellow precipitate was observed. The reaction was stirred at 0° C. for ½ h, poured into a 0° C. solution of 50% aq $NH_4OH$ and stirred overnight. The aqueous layer was separated, acidified with concentrated HCl and extracted with $Et_2O$ (2x). The combined $Et_2O$ layers were washed with saturated $Na_2S_2O_3$ (aq), passed through silica gel and dried ($MgSO_4$). The solvent was removed in vacuo affording 6 g of a light yellow solid that was recrystallized from hot ether/hexane affording 5 g (53%) of product as a light beige solid: mp 162°–164° C.

Elemental Analysis: C H N

Calculated 37.39 1.74 4.84
Found 37.41 1.77 4.78

EXAMPLE 25

3-Pyridinecarboxylic acid,
5-methoxy-2,6-bis(trifluoromethyl)-,methyl ester.

This compound was prepared as described in Example 21; 3.27 g (0.0113 mol) of product of Example 24 was treated with 10.64 g (0.113 mol) of KF·2H$_2$O and 1.7 g (0.8 mL, 0.012 mol) of CH$_3$I in 25 mL of DMF for 24 hours affording 3.15 g of a light yellow solid. The solid was recrystallized from hot ether/hexane affording 2.68 g (78%) of product as a white solid: mp 49°–51° C.

Elemental Analysis: C H N
Calculated 39 62 2.33 4.62
Found 39.80 2.42 4.58

EXAMPLE 26

3-Pyridinecarboxylic acid,
6-(difluoromethyl)-5-ethoxy-4-hydroxy-2-(trifluoromethyl)-, ethyl ester.

This compound was prepared as described in Example 19; 17.48 g (0.05 mol) of product of Example 23, 10.12 g (14. mL, 0.1 mol) of triethylamine and 0.9 g of 10% Pd/C (52% H$_2$O) at 50° C. were treated with H$_2$(g) for 24 hours affording 10 g of a light brown oil. The oil was purified by HPLC in 20% ethyl acetate:cyclohexane affording 8.32 g of product (50%) as a light yellow oil. A sample for elemental analysis was Kugelrohr distilled at 82°–85° C. (0.4 mm Hg) affording a semi-solid clear oil: mp 20°–23° C.

Elemental Analysis: C H N
Calculated 43.78 3.67 4.25
Found 44.00 3.79 4.18

EXAMPLE 27

3-Pyridinecarboxylic acid,
6-difluoromethyl-5-ethoxy-4-hydroxy-2-(trifluoromethyl)-,ethyl ester.

This compound was prepared as in Example 16; 3.83 g (0.0116 mol) of product of Example 26, 1.6 g (0.0116 mol) of K$_2$CO$_3$ and 5.1 g (0.03 mol) of 2-iodopropane in 10 mL of acetone were refluxed for 24 hours affording 4.48 g of a light orange oil. The oil was Kugelrohr distilled affording 3.78 g (88%) of product as a colorless liquid: bp 100°–120° C. (0.9 mm Hg); n$_D^{25}$ 1.4406.

Elemental Analysis: C H N
Calculated 48.52 4.89 3.77
Found 48.55 4.89 3.75

EXAMPLE 28

3-Pyridinecarboxylic acid,
5-ethoxy-4-ethyl-2,6-bis(trifluoromethyl).

To a solution of 1.8 g (0.005 mol) of product of Example 13 in 25 mL of dry CH$_2$Cl$_2$ was added 10 mL (0.01 mol) of 1.0 M BBr$_3$ solution in dry CH$_2$Cl$_2$. The reaction mixture was stirred at room temperature overnight then poured into 0° C. H$_2$O and stirred at room temperature for 1 hour. The CH$_2$Cl$_2$ phase was separated, the aqueous layer extracted with CH$_2$Cl$_2$ (2x) and the combined organics were dried (Na$_2$SO$_4$) and reduced in vacuo. The residue was dissolved in Et$_2$O and extracted with 10% NaOH (2x) and H$_2$O (2x); and combined aqueous layers were acidified with concentrated HCl and extracted with Et$_2$O (2x). The Et$_2$O layers were combined and concentrated in vacuo. The residue was Kugelrohr distilled affording 0.61 g (38%) of product as a beige solid: bp 100°–105° C. (0.6 mm Hg); mp 100°–104° C.

Elemental Analysis: C H N
Calculated 43.51 3.35 4.23
Found 43.27 3.38 4.16

EXAMPLE 29

3-Pyridinecarboxylic acid,
6-(difluoromethyl)-5-methoxy-4-(1-methylethoxy)-2-(trifluoromethyl)-,methyl ester.

To a solution of 5.8 g (0.02 mol) of product of Example 19 in 40 mL of DMF was added 1.88 g (0.02 mol) of KF·2H$_2$O followed by 10.2 g (6 mL, 0.06 mol) of 2-iodopropane. The reaction mixture was stirred at room temperature for 28 hours, poured into H$_2$O and extracted with Et$_2$O. The Et$_2$O layer was washed with 5% NaOH, H$_2$O (3x), dried (MgSO$_4$) and the solvent was removed in vacuo affording a light orange liquid. The crude material was Kugelrohr distilled affording 3.94 g (57%) of product as a colorless oil: bp 85°–90° C. (0.6 mm Hg); n$_D^{25}$ 1.4399.

Elemental Analysis: C H N Calculated 45.49 4.11 4.08
Found 45.68 4.15 4.12

EXAMPLE 30

3-Pyridinecarboxylic acid,
6-(chlorodifluoromethyl)-5-ethoxy-4-(1-methylethoxy)-2-(trifluoromethyl)-,ethyl ester.

This compound was prepared as described in Example 16; 4.22 g (0.0115 mol) of product of Example 23, 1.95 g (0.0115 mol) of K$_2$CO$_3$ and 5.1 g (3 mL, 0.03 mol) of 2-iodopropane in 30 mL of acetone were refluxed for 24 hours affording 4.47 g of a thick brown oil. The oil was purified by Kugelrohr distillation affording 3.74 g (80%) of a colorless oil: bp 85°–39° C. (0.55 mm Hg); n$_D^{25}$ 1.4399.

Elemental Analysis: C H N Cl
Calculated 44.40 4.22 3.45 8.74
Found 44.44 4.29 3.40 8.75

EXAMPLE 31

3-Pyridinecarboxylic acid,
6-(chlorodifluoromethyl)-5-methoxy-4-(1-methlethoxy)-2-(trifluoromethyl)-,methyl ester (0.7 hydrate)

This compound was prepared as described in Example 29; 6.7 g (0.02 mol) of product of Example 15, 1.88 g (0.02 mol) of KF·2H$_2$O and 13.6 g (8 mL, 0.08 mol) of 2-iodopropane in 40 mL of DMF were stirred at room temperature for 1 week affording 0.72 g (10%) of product as a colorless oil: bp 70° C. (0.3 mm Hg); n$_D^{25}$ 1.4409.

Elemental Analysis: C H N
Calculated 40.00 3.72 3.59
Found 39.77 3.36 3.56

Further compounds of this invention were prepared by methods similar to those set out in detail in the preceding Examples. These compounds are shown in the following Table 1, along with a physical property for each.

TABLE 1

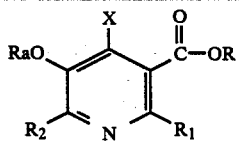

| Example | $R_1$ | R | X | $R_a$ | $R_2$ | Mp(°C.) | $n_D^{25}$ |
|---|---|---|---|---|---|---|---|
| 32 | $CF_3$ | $CH_2CH_3$ | $-\overset{O}{\underset{\|}{C}}OCH_3$ | $CH_2CH_3$ | $CF_3$ | 36.0–38.0 | |
| 33 | $CF_3$ | $CH_2CH_3$ | $-\overset{O}{\underset{\|}{C}}OCH_2CH_3$ | $CH_2CH_3$ | $CF_3$ | 32.0–34.0 | |
| 34 | $CF_3$ | $CH_2CH_3$ | [(4-methylphenyl)sulfonyl]oxy | $CH_2CH_3$ | $CF_2Cl$ | 74.0–76.0 | |
| 35 | $CF_3$ | $CH_2CH_3$ | H | $CH_2CH_3$ | $CF_2Cl$ | | 1:4519 |
| 36 | $CF_3$ | $CH_2CH_3$ | —$OCH_3$ | $CH_2CH_3$ | $CF_2Cl$ | 53.0–54.5 | |
| 37 | $CF_3$ | $CH_3$ | $O^-[(CH_3)_2CHNH_2CH(CH_3)_2]^+$ | $CH_3$ | $CF_3$ | 109.0–110.0 | |
| 38 | $CF_3$ | $CH_3$ | benzoyloxy | $CH_3$ | $CF_3$ | 101.0–103.0 | |

EXAMPLE 39

3-Pyridinecarboxylic acid, 5-methoxy-4-ethyl-2-trifluoromethyl-6-difluoromethyl-, methyl ester.

A mixture of 35 g of 3-carbethoxy-6-(difluoromethyl)-4-ethyl-2-(trifluoromethyl)-5-pyridinecarboxylic acid, (a known compound; see Example 26 of European Patent Publication No. 133,612) and 60 ml of $SOCl_2$ was refluxed overnight. The $SOCl_2$ was then removed in vacuo. This was diluted with 10 ml acetone and added to a slurry of 14.3 g of $NaN_3$, 25 ml of $H_2O$ and 90 ml of acetone. Vigorous gas evolution occurred and the reaction became exothermic. The mixture was stirred until the reaction returned to RT, then was diluted with 300 ml $H_2O$ and extracted with $CHCl_3$. Normal workup afforded the 5-amino intermediate as a tan solid. Yield. 30.93 g (96%), mp=92°–94° C.

To a RT solution of 5.09 g of $CuBr_2$, 2.94 g of t-BuONO and 70 ml $CH_3CN$ was added a solution of 6.0 g of the 5-amino intermediate in 5 ml $CH_3CN$. This was stirred 2 hours at RT. The reaction mixture was poured into 200 ml of 10% HCl and extracted with $CHCl_3$. Normal workup gave a yield of 7.59 g of the 5-bromo intermediate. This material was kugelrohr distilled at 125° C. at 1 torr. Yield=6.35 g (89%).

A solution of 3.24 g of the 5-bromo intermediate and methanolic sodium methoxide prepared from 1.5 g of Na and 50 ml of MeOH was stirred at reflux for 5] hours, following the reaction by GC. The reaction mixture was poured into $H_2O$ and extracted with $CHCl_3$ followed by normal workup.

The resulting material was passed through a short plug of silica gel with 5% EtOAc/cyclohexane, and was then kugelrohr distilled (120° C. at 1 torr) to give the desired product as a white solid. Yield=1.70 g (63%), mp 40°–42° C.

Elemental Analysis: C H N
Calculated 46.02 3.86 4.47
Found 46.19 3.87 4.43

EXAMPLE 40

3-Pyridinecarboxylic acid, 5-methoxy-4-isopropyl-2-trifluoromethyl-6-difluoromethyl-, methyl ester.

This material was prepared using a method similar to that of Example 39 as a colorless oil, $n_D^{25}$ 1.449.
Elemental Analysis: C H N
Calculated 49.27 4.73 4.10
Found 49.36 4.78 4.07

PRE-EMERGENT HERBICIDE EXAMPLES

As noted above, many of the compounds of this invention have been found to be effective as herbicides, usually as pre-emergent herbicides. Table 2 summarizes results of tests conducted to determine the pre-emergent herbicidal activity of the compounds of this invention on common weeds.

The pre-emergent tests are conducted as follows:

Top soil is placed in aluminum pans and compacted to a depth of 0.95 to 1.27 cm. from the top of the pan. On the top of the soil is placed a predetermined number of seeds or vegetative propagules of various plant species. The soil required to level fill the pans after seeding or adding vegetative propagules is weighed into a pan. A known amount of the active ingredient applied in acetone as a solvent is thoroughly mixed with the soil, and the herbicide/soil mixture is used as a cover layer for prepared pans. In Table 2 below the amount of active ingredient is equal to the rate of 11.2 kg/ha. After treatment, the pans are moved into a greenhouse bench where they are watered from below as needed to give adequate moisture for germination and growth.

Approximately 10–14 days (usually 11 days) after seeding and treating, the pans are observed and the results recorded. In some instances, an observation is made approximately 24–28 days after seeding and treating, and these observations are indicated in the following tables by an asterisk (*) immediately following the Example number.

Table 2 below summarizes the results of the pre-emergent herbicidal activity tests of compounds of this invention in weeds.

The herbicidal rating is obtained by means of a fixed scale based on the percent inhibition of each plant species. The symbols in the Table are defined as follows:

| % Inhibition | Rating |
|---|---|
| 0-24 | 0 |
| 25-49 | 1 |
| 50-74 | 2 |
| 75-100 | 3 |
| Not planted | — |
| Species planted, no data | N |

WEED-PLANT HERBICIDE ACTIVITY

The plant species usually regarded as weeds which are utilized in one set of tests, the data for which are shown in Table 2, are identified by letter headings above the columns in accordance with the following legend:

| | |
|---|---|
| A - Canada Thistle* | E - Common Lambsquarters |
| B - Cocklebur | F - Pennsylvania Smartweed |
| C - Velvetleaf | G - Yellow Nutsedge* |
| D - Morning Glory | H - Quackgrass* |
| | I - Johnsongrass* |
| | J - Downy Brome |
| | K - Barnyardgrass |

*Grown from vegetative propagules

TABLE 2
PRE-EMERGENCE HERBICIDE ACTIVITY FOR WEEDS

| Example No. | kg/ha | A | B | C | D | E | F | G | H | I | J | K |
|---|---|---|---|---|---|---|---|---|---|---|---|---|
| 1 | 11.2 | 0 | 0 | 1 | 2 | 3 | 1 | 0 | 0 | 0 | 0 | 0 |
| 2 | 11.2 | 0 | 0 | 0 | 0 | 0 | 0 | 0 | 0 | 0 | 0 | 0 |
| 3 | 11.2 | 1 | 1 | 0 | 1 | 3 | 2 | 3 | 3 | 1 | 2 | 1 |
| 3* | 11.2 | 2 | 0 | 0 | 0 | 3 | 2 | 2 | 3 | 1 | 2 | 1 |
| 4 | 11.2 | 0 | 0 | 0 | 0 | 0 | 0 | 0 | 0 | 0 | 0 | 0 |
| 5 | 11.2 | 0 | 0 | 0 | 0 | 0 | 0 | 0 | 0 | 0 | 0 | 0 |
| 6 | 11.2 | 0 | 0 | 0 | 1 | 3 | — | 0 | 0 | 3 | 0 | 0 |
| 6* | 11.2 | 0 | 0 | 0 | 0 | 3 | — | 0 | 0 | 0 | 0 | 0 |
| 7 | 11.2 | 0 | 0 | 0 | 0 | 3 | — | 0 | 0 | 0 | 0 | 0 |
| 8 | 11.2 | 3 | 1 | 3 | 3 | 3 | — | 0 | 1 | 3 | 1 | 2 |
| 9 | 11.2 | 0 | 0 | 0 | 0 | 3 | — | 0 | 0 | 0 | 2 | 0 |
| 10 | 11.2 | 3 | 3 | 3 | 3 | 3 | — | 1 | 3 | 2 | 2 | 3 |
| 10* | 11.2 | 3 | 3 | 3 | 3 | 3 | — | 0 | 0 | 1 | 2 | 3 |
| 11 | 11.2 | 0 | 0 | 0 | 2 | 0 | — | 0 | 0 | 0 | 3 | 3 |
| 12 | 11.2 | 0 | 0 | 0 | 0 | 3 | — | 0 | 0 | 0 | 3 | 3 |
| 13 | 11.2 | 3 | 0 | 2 | 3 | 3 | — | 1 | 3 | 3 | 3 | 3 |
| 14 | 11.2 | 0 | 0 | 0 | 0 | 3 | — | 0 | 0 | 0 | 0 | 0 |
| 15 | 11.2 | 0 | 0 | 0 | 0 | 3 | — | 0 | 0 | 0 | 0 | 1 |
| 16 | 11.2 | 0 | 0 | 0 | 0 | 1 | — | 0 | 0 | 0 | 0 | 0 |
| 17 | 11.2 | 0 | 0 | 0 | 0 | 1 | — | 0 | 0 | 0 | 3 | 2 |
| 18 | 11.2 | 0 | 0 | 0 | 0 | 3 | — | 0 | 3 | 2 | 3 | 2 |
| 19 | 11.2 | 0 | 0 | 0 | 3 | 3 | — | 0 | 0 | 0 | 1 | 0 |
| 20 | 11.2 | 0 | 0 | 0 | 0 | 0 | — | 0 | 0 | 0 | 0 | — |
| 21 | 11.2 | 0 | 1 | 0 | 0 | 0 | — | 0 | 3 | 0 | 3 | 3 |
| 22 | 11.2 | 3 | 2 | 3 | 3 | 3 | — | 0 | 0 | 0 | 1 | 1 |
| 23 | 11.2 | 0 | 0 | 0 | 0 | 0 | — | 0 | 0 | 0 | 0 | 0 |
| 24 | 11.2 | 2 | 0 | 0 | 0 | 0 | — | 0 | 0 | 0 | 0 | 0 |
| 25 | 11.2 | 0 | 0 | 0 | 0 | 0 | — | 0 | 0 | 0 | 0 | 0 |
| 26 | 11.2 | 0 | 0 | 2 | 0 | 3 | — | 0 | 0 | 0 | 0 | 0 |
| 27 | 11.2 | 3 | 0 | 0 | 2 | 3 | 2 | 0 | 3 | 3 | 3 | 3 |
| 27* | 11.2 | 2 | 3 | 0 | 3 | 3 | 3 | 0 | 3 | 3 | 3 | 3 |
| 28 | 11.2 | 3 | 0 | 0 | 0 | 2 | 0 | 0 | 0 | 0 | 0 | 0 |
| 28* | 11.2 | 0 | 0 | 0 | 0 | 2 | 0 | 0 | 0 | 0 | 0 | 0 |
| 29 | 11.2 | 1 | 0 | 0 | 0 | 1 | 0 | 0 | 0 | 0 | 2 | 1 |
| 29* | 11.2 | 0 | 0 | 0 | 0 | 1 | 1 | 0 | 2 | 0 | 3 | 3 |
| 30 | 11.2 | 0 | 0 | 0 | 1 | 3 | 0 | 0 | 3 | 0 | 3 | 3 |
| 31 | 11.2 | 0 | 0 | 0 | 0 | 3 | 0 | 0 | 3 | 0 | 3 | 3 |
| 32 | 11.2 | 3 | 0 | 0 | 1 | 2 | 1 | 0 | 0 | 0 | 0 | 3 |
| 33 | 11.2 | 0 | 0 | 0 | 0 | 0 | 0 | 0 | 0 | 0 | 0 | 1 |
| 34 | 11.2 | 1 | 2 | 0 | 0 | 0 | 0 | 1 | 0 | 0 | 0 | 0 |
| 35 | 11.2 | 0 | 1 | 1 | 1 | 3 | 0 | 0 | 0 | 0 | 3 | 1 |
| 36 | 11.2 | 1 | 0 | 0 | 2 | 3 | 3 | 0 | 3 | 0 | 3 | 3 |
| 37 | 11.2 | 0 | 0 | 0 | 0 | 3 | 0 | 0 | 0 | 0 | 0 | 0 |
| 38 | 11.2 | 0 | 0 | 0 | 0 | 1 | 0 | 0 | 0 | N | 0 | 2 |
| 39 | 11.2 | 0 | 0 | 1 | 3 | 1 | 1 | 2 | 3 | — | 3 | 3 |

TABLE 2-continued
PRE-EMERGENCE HERBICIDE ACTIVITY FOR WEEDS

| Example No. | kg/ha | A | B | C | D | E | F | G | H | I | J | K |
|---|---|---|---|---|---|---|---|---|---|---|---|---|
| 40 | 11.2 | 0 | 0 | 0 | 0 | 3 | 0 | 0 | 0 | 0 | 0 | 0 |

POST-EMERGENT HERBICIDE EXAMPLES

The post-emergence herbicidal activity of some of the various compounds of this invention was demonstrated by greenhouse testing in the following manner. Top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, except for the control pans, is removed individually to a spraying chamber and sprayed by means of an atomizer, operating at a spray pressure of 170.3 kPa (10 psig) at the application rates noted. In the spray solution is an amount of an emulsifying agent mixture to give a spray solution or suspension which contains about 0.4% by weight of the emulsifier. The spray solution or suspension contains a sufficient amount of the candidate chemical in order to give application rates of the active ingredient corresponding to those shown in the Tables while applying a total amount of solution or suspension equivalent to 18% L/Ha (200 gallons/acre). The pans were returned to the greenhouse and watered as before and the injury to the plants as compared to the control is observed at approximately 10-14 days (usually 11 days) and in some instances observed again at 24-28 days (usually 25 days) after spraying. These latter observations are designated by an asterisk (*) following the column of example numbers in the Table.

The post-emergent herbicidal acitvity index used in Tables 4 and 5 is as follows:

| Plant Response | Index |
|---|---|
| 0-24% inhibition | 0 |
| 25-49% inhibition | 1 |
| 50-74% inhibition | 2 |
| 75-99% inhibition | 3 |
| 100% inhibition | 4 |
| Species not planted | — |
| Species planted, no data | N |

TABLE 3
POST-EMERGENCE ACTIVITY FOR WEEDS

| Example No. | kg/ha | A | B | C | D | E | F | G | H | I | J | K |
|---|---|---|---|---|---|---|---|---|---|---|---|---|
| 1 | 11.2 | N | 1 | 0 | 2 | 0 | 1 | 0 | 0 | 0 | 0 | 1 |
| 2 | 11.2 | N | 2 | 0 | 1 | 0 | 0 | 0 | 0 | 0 | 0 | 0 |
| 3 | 11.2 | 0 | 2 | 0 | 2 | 1 | 1 | 1 | 0 | 0 | 0 | 1 |
| 3* | 11.2 | 0 | 2 | 1 | 2 | 1 | 1 | 1 | 0 | 0 | 0 | 0 |
| 4 | 11.2 | 0 | 0 | 0 | 0 | 0 | 0 | 0 | 1 | 0 | 0 | 2 |
| 5 | 11.2 | 0 | 0 | 0 | 0 | 0 | 0 | 0 | 0 | 0 | 0 | 0 |
| 6 | 11.2 | 0 | 0 | 0 | 2 | 4 | — | 0 | 0 | 0 | 0 | 0 |
| 6* | 11.2 | 0 | 0 | 0 | 2 | 4 | — | 0 | 0 | 0 | 0 | 0 |
| 7 | 11.2 | 0 | 0 | 0 | 1 | 0 | — | 0 | 0 | 0 | 0 | 0 |
| 8 | 11.2 | 3 | 3 | 3 | 3 | 4 | — | 0 | 0 | 0 | 0 | 2 |
| 9 | 11.2 | 0 | 0 | 0 | 0 | 0 | — | 0 | 0 | 0 | 0 | 0 |

TABLE 3-continued
POST-EMERGENCE ACTIVITY FOR WEEDS

| Example No. | kg/ha | A | B | C | D | E | F | G | H | I | J | K |
|---|---|---|---|---|---|---|---|---|---|---|---|---|
| 10 | 11.2 | 3 | 3 | 3 | 3 | 4 | — | 0 | 0 | 0 | 0 | 1 |
| 10* | 11.2 | 4 | 4 | 3 | 4 | 4 | — | 1 | 0 | 0 | 0 | 1 |
| 11 | 11.2 | 0 | 0 | 0 | 1 | 1 | — | 0 | 0 | 0 | 0 | 0 |
| 12 | 11.2 | 0 | 0 | 0 | 0 | 0 | — | 0 | 0 | 0 | 0 | 0 |
| 13 | 11.2 | 0 | 0 | 0 | 0 | 0 | — | 0 | 0 | 0 | 0 | 0 |
| 14 | 11.2 | 4 | 1 | 0 | 2 | 1 | — | 0 | 0 | 0 | 0 | 1 |
| 15 | 11.2 | 2 | 2 | 0 | 1 | 1 | — | 0 | 0 | 0 | 0 | 0 |
| 16 | 11.2 | 0 | 1 | 0 | 0 | 1 | — | 0 | 0 | 0 | 0 | 0 |
| 17 | 11.2 | 0 | 0 | 0 | 0 | 0 | — | 0 | 0 | 0 | 0 | 0 |
| 18 | 11.2 | 0 | 0 | 0 | 0 | 0 | — | 0 | 0 | 0 | 0 | 0 |
| 19 | 11.2 | 1 | 1 | 0 | 0 | 0 | — | 0 | 0 | 0 | 0 | 0 |
| 20 | 11.2 | 0 | 1 | 0 | 2 | 0 | — | 0 | 0 | 0 | 0 | 0 |
| 20* | 11.2 | 0 | 1 | 0 | 2 | 0 | — | 0 | 0 | 0 | 0 | 0 |
| 21 | 11.2 | 0 | 0 | 0 | 0 | 0 | — | 0 | 0 | 0 | 0 | 0 |
| 22 | 11.2 | 1 | 2 | 2 | 2 | 3 | — | 0 | 0 | 0 | 0 | 0 |
| 22* | 11.2 | 2 | 4 | 4 | 3 | 4 | — | 0 | 0 | 0 | 0 | 0 |
| 23 | 11.2 | 0 | 2 | 0 | 1 | 1 | — | 0 | 0 | 0 | 0 | 0 |
| 23* | 11.2 | 0 | 2 | 0 | 1 | 1 | — | 0 | 0 | 0 | 0 | 0 |
| 24 | 11.2 | 0 | 1 | 0 | 1 | 1 | — | 0 | 0 | 0 | 0 | 0 |
| 25 | 11.2 | 0 | 0 | 0 | 0 | 0 | — | 0 | 0 | 0 | 0 | 0 |
| 26 | 11.2 | 0 | 2 | 1 | 1 | 0 | — | 0 | 0 | 0 | 0 | 0 |
| 26* | 11.2 | 0 | 2 | 1 | 1 | 1 | — | 0 | 0 | 0 | 0 | 0 |
| 27 | 11.2 | 0 | 0 | 0 | 0 | 0 | — | 0 | 0 | 0 | 0 | 0 |
| 28 | 11.2 | N | 0 | 1 | 0 | 0 | 0 | 0 | 0 | 0 | 0 | 0 |
| 29 | 11.2 | 0 | 0 | 0 | 0 | 0 | 0 | 0 | 0 | 0 | 0 | 0 |
| 30 | 11.2 | 0 | 0 | 0 | N | 0 | 0 | 0 | 0 | 0 | 0 | 0 |
| 31 | 11.2 | N | 0 | 0 | 0 | N | 0 | 0 | 0 | 0 | 0 | 0 |
| 32 | 11.2 | 0 | 0 | 0 | 0 | 0 | 0 | 0 | 0 | 0 | 0 | 0 |
| 33 | 11.2 | 0 | 0 | 0 | 0 | 0 | 0 | 0 | 0 | 0 | 0 | 0 |
| 34 | 11.2 | 0 | 2 | 0 | 1 | 0 | 0 | 0 | 0 | 0 | 0 | 0 |
| 34* | 11.2 | 0 | 2 | 0 | 1 | 0 | 0 | 0 | 0 | 0 | 0 | 0 |
| 35 | 11.2 | 0 | 0 | 0 | 0 | N | 0 | 0 | 0 | 0 | 0 | 0 |
| 36 | 11.2 | 0 | 0 | 0 | 0 | N | 0 | 0 | 0 | 0 | 0 | 0 |
| 37 | 11.2 | 0 | 0 | 0 | 0 | 0 | 0 | 0 | 0 | 0 | 0 | 0 |
| 38 | 11.2 | 0 | 1 | 0 | 2 | 1 | 0 | 0 | 0 | 0 | 0 | 2 |
| 39 | 11.2 | 0 | 0 | 0 | 0 | 0 | 0 | 0 | 0 | 0 | 0 | 0 |
| 40 | 11.2 | 0 | 0 | 0 | 0 | 0 | 0 | 0 | 0 | — | 0 | 0 |

The above tables illustrate one aspect of the present invention, that is, the use of the compounds of the invention to kill or injure undesirable plants, e.g., weeds.

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetabe oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan), and polyoxyethylene derivatives of castor oil. Preferred dispersants are methyl cellulose, polyvinyl alcohol, sodium lignin sulfonates, polyoxyethylene/polyoxypropylene block copolymers, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usualy of mineral origin such as the natural clays, diatomaceous earth and synthetic minerals derived from silica and the ike. Examples of such extenders include kaolinites, bentonite, attapulgite clay and synthetic magnesium silicate. The wettable powders compositions of this invention usually contain from above 0.5 to 60 parts (preferably from 5-20 parts) of active ingredient, from about 0.25 to to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to to 2.0 parts of the solid inert extender can be replaced by a corrosion inhibitor or antifoaming agent or both.

Other formulations include dust concentrates comprising from 0.1 to 60% by weight of the active ingredient on a suitable extender; these dusts may be diluted for application at concentrations within the range of from about 0.1 to 10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1 to 60% (preferably 5 to 50%) by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include chlorinated solvents, dimethylformamide, dimethylsulfoxide, N-methylpyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5-60 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particules such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like such as:

HETEROCYCLIC NITROGEN/SULFUR DERIVATIVES

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-a:2',1'-c)-pyrazidiinium salt
5-Bromo-3-isopropyl-6-methyluracil 1,1'-Dimethyl-4,4'-bipyridinium
2-(4-isopropyl-4-methyl-5-oxo-2-imidazolin-2-yl)-3-quinolinecarboxylic acid
Isopropylamine salt of 2-(4-isopropyl-4-methyl-5-oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate

UREAS

N-(4-chlorophenoxy) phenyl-N,N-dimethylurea
N,N-dimethyl-N'-(3-chloro-4-methylphenyl) urea
3-(3,4-dichlorophenyl)-1,1-dimethylurea
1,3-Dimethyl-3-(2-benzothiazolyl) urea
3-(p-Chlorophenyl)-1,1-dimethylurea
1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate

CARBAMATES/THIOLCARBAMATES

2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate

ACETAMIDES/ACETANILIDES/ANILINES/AMIDES

2-Chloro-N,N-diallylacetamide
N,N-dimethyl-2,2-diphenylacetamide
N-(2,4-dimethyl-5-[[(trifluoromethyl)sulfonyl] amino]-phenyl]acetamide
N-Isopropyl-2-chloroacetanilide
2',6'-Diethyl-N-methoxymethyl-2-chloroacetanilide
2'-Methyl-6'-ethyl-N-(2-methoxyprop-2-yl)-2chloroacetanilide
α,α,α-Trifluoro-2,6-dinitro-N,N-dipropyl-p-toluidine
N-(1,1-dimethylpropynyl)-3,5-dichlorobenzamide

ACIDS/ESTERS/ALCOHOLS 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2chloro-4-(trifluoromethyl)phenoxy]-2-nitrobenzoate.
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate.

ETHERS 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methylsulfonyl 2-nitrobenzamide
1'-(Carboethoxy) ethyl 5-[2-chloro-4-(trifluoromethyl)-phenoxy]-2-nitrobenzoate

MISCELLANEOUS 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methylethyl)-2-(2-methylphenylmethoxy)-,exo- Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | Weight Percent |
|---|---|
| I. Emulsifiable Concentrates | |
| A. Compound of Example No. 3 | 11.0 |
| Free acid of complex organic phosphate or aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered | 1.11 |

| | Weight Percent |
|---|---|
| trademark of Union Carbide Corp.) | |
| C9 aromatics | 5.34 |
| Monochlorobenzene | 76.96 |
| | 100.00 |
| B. Compound of Example No. 14 | 25.00 |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |
| II. Flowables | |
| A. Compound of Example No. 24 | 25.00 |
| Methyl cellulose | 0.3 |
| Silica Aerogel | 1.5 |
| Sodium lignosulfonate | 3.5 |
| Sodium N-methyl-N-oleyl taurate | 2.0 |
| Water | 67.7 |
| | 100.00 |
| B. Compound of Example No. 18 | 45.0 |
| Methyl cellulose | .3 |
| Silica aerogel | 1.5 |
| Sodium lignosulfonate | 3.5 |
| Sodium N-methyl-N-oleyl taurate | 2.0 |
| Water | 47.7 |
| | 100.00 |
| III. Wettable Powders | |
| A. Compound of Example No. 5 | 25.0 |
| Sodium lignosulfonate | 3.0 |
| Sodium N-methyl-N-oleyl-taurate | 1.0 |
| Amorphous silica (synthetic) | 71.0 |
| | 100.00 |
| B. Compound of Example 21 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 6 | 10.0 |
| Sodium lignosulfonate | 3.0 |
| Sodium N-methyl-N-oleyl-taurate | 1.0 |
| Kaolinite clay | 86.0 |
| | 100.00 |
| IV. Dusts | |
| A. Compound of Example No. 13 | 2.0 |
| Attapulgite | 98.0 |
| | 100.00 |
| B. Compound of Example No. 10 | 60.0 |
| Montmorillonite | 40.0 |
| | 100.00 |
| C. Compound of Example No. 23 | 30.0 |
| Ethylene glycol | 1.0 |
| Bentonite | 69.0 |
| | 100.00 |
| D. Compound of Example No. 9 | 1.0 |
| Diatomaceous earth | 99.0 |
| | 100.00 |
| V. Granules | |
| A. Compound of Example No. 16 | 15.0 |
| Granular attapulite (20/40 mesh) | 85.0 |
| | 100.00 |
| B. Compound of Example No. 10 | 30.0 |
| Diatomaceous earth (20/40) | 70.0 |
| | 100.00 |
| C. Compound of Example No. 7 | 1.0 |
| Ethylene glycol | 5.0 |
| Methylene blue | 0.1 |
| Pyrophyllite | 93.9 |
| | 100.00 |
| D. Compound of Example No. 4 | 5.0 |
| Pyrophyllite (20/40) | 95.0 |
| | 100.00 |

When operating in accordance with the present invention, effective amounts of the compounds of this invention are applied to the soil containing the seeds, or vegetative propagules or may be incorporated into the soil media in any comvenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective preemergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or media in which vegetation may take root and grow, arid includes not only earth but also compost, manure, muck, humus, sand, and the like, adapted to support plant growth.

Although the invention is described with respect to specific modifications, the details thereof are not to be construed as limitations.

We claim:

1. A compound represented by the formula

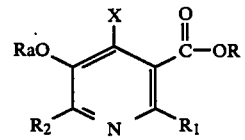

wherein:
R is selected from the group consisting of hydrogen, alkyl, alkenyl, alkynyl, $C_1$–$C_7$ haloalkyl and $C_3$–$C_7$ haloalkenyl;

$R_1$ and $R_2$ are independtly selected from the group consisting of fluorinated methyl and chlorofluorinated methyl radicals;

Ra is selected from the group consisting of lower alkyl, hydrogen and phenyl optionally substituted with one or more groups selected from the group consisting of methyl, methoxy, and chloro; and X is selected from the group consisting of hydrogen, hydroxy, alkoxy; phenylsulfonloxy, phenylcarbonyloxy, phenyloxyacetyloxy wherein phenyl is optionally substituted with one or more groups selected from the group consisting of methyl, methoxy, or chloro;

trialkylsilyl, lower alkyl, alkoxycarbonylalkoxy, alkoxycarbonyl, and —OZ wherein Z is a monovalent cation forming a salt of the hydroxy compound;

wherein the termalkyl and its combining forms mean $C_1$–$C_7$ alkyl, and wherein alkenyl and alkynyl mean $C_3$–$C_7$ alkenyl and $C_3$–$C_7$ alkynyl, respectively.

$C_3$–$C_7$ alkenyl and $C_3$–$C_7$ alkynyl, respectively in an admixture with an inert carrier.

2. A compound according to claim 1 wherein $R_1$ is trifluoromethyl and $R_2$ is selectred from trifluoromethyl, difluoromethyl, and chlorodifluoromethyl.

3. A compound according to claim 2 wherein R is selected from methyl and ethyl.

4. A compound according to claim 3 wherein Ra is selected from methyl, ethyl, and 4-chlorophenyl.

5. A compound according to claim 4 wherein X is selected from chlorophenoxyacetyloxy, lower alkyl, and lower alkoxy.

6. An herbicidal composition comprising as active ingredient an effective amount of a compound represented by the formula

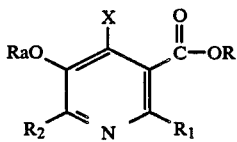

wherein:

R is selected from the group consisting of hydrogen, alkyl, alkenyl, alkynyl, $C_1$–$C_7$ haloalkyl and $C_3$–$C_7$ haloalkenyl;

$R_1$ and $R_2$ are indepently selected from the group consisting of fluorinated methyl and chloroflluorinated methyl radicals;

Ra is selected from the group consisting of lower alkyl, hydrogen and phenyl optionally substituted with one or more groups selected from the group consisting of methyl, methoxy, and chloro; and X is selected from the group consisting of hydrogen, hydroxy, alkoxy; phenylsulfonyloxy, phenylcarbonyloxy, phenyloxyacetyloxy wherein phenyl is optionally substituted with one or more groups selected from the group consisting of methyl, methoxy, or chloro; trialkylsilyl, lower alkyl, alkoxycarbonylalkoxy, alkoxycarbonyl, and —OZ wherein Z is a monovalent cation forming a salt of the hydroxy compound;

wherein the term alkyl and its combining forms mean $C_1$–$C_7$ alkyl, and wherein alkenyl and alkynyl mean $C_3$–$C_7$ alkynyl, respectively in admixture with an inert carrier.

7. A composition according to claim 6 wherein $R_1$ is trifluoromethyl and $R_2$ is selected from trifluoromethyl, difluoromethyl, and chlorodifluoromethyl.

8. A composition according to claim 7 wherein R is selected from methyl and ethyl.

9. A composition according to claim 8 wherein Ra is selected from methyl, ethyl, and 4-chlorophenyl.

10. A composition according to claim 9 wherein X is selected from chlorophenoxyacetyloxy, lower alkyl, and lower alkoxy.

11. A method of controlling undersirable plants comprising applying to the plant locus an effective amount of a compound represented by the formula

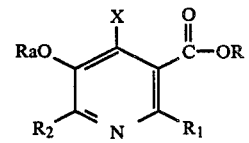

wherein:

R is selected from the group consisting of hydrogen, alkyl, alkenyl, alkynyl, $C_1$–$C_7$ haloalkyl and $C_3$–$C_7$ haloalkenyl;

$R_1$ and $R_2$ are indepently selected from the group consisting of fluorinated methyl and chlorofluorinated methyl radicals;

Ra is selected from the group consisting of lower alkyl, hydrogen and phenyl optionally substituted with one or more groups selected from the group consisting of methyl, methoxy, and chloro; and X is selected from the group consisting of hydrogen, hydroxy, alkoxy; phenylsulfonyloxy, phenylcarbonyloxy, phenyloxyacetyloxy wherein phenyl is optionally substituted with one or more groups selected from the group consisting of methyl, methoxy, or chloro; trialkylsilyl, lower alkyl, alkoxycarbonylalkoxy, alkoxycarbonyl, and —OZ wherein Z is a monovalent cation forming a salt of the hydroxy compound;

wherein the term alkyl and its combining forms mean $C_1$–$C_7$ alkyl, and wherein alkenyl and alkynyl mean $C_3$–$C_7$ alkynyl, respectively.

12. A method according to claim 11 wherein $R_1$ trifluoromethyl and $R_2$ is selected from trifluoromethyl, difluoromethyl, and chlorodifluoromethyl.

13. A method according to claim 12 wherein R is selected from methyl and ethyl.

14. A method according to claim 13 wherein Ra is selected from methyl, ethyl, and 4-chlorophenyl.

15. A method according to claim 14 wherein X is selected from chlorophenoxyacetyloxy, lower alkyl, and lower alkoxy.

* * * * *